United States Patent
Yamaguchi et al.

(10) Patent No.: US 10,183,094 B2
(45) Date of Patent: Jan. 22, 2019

(54) BIODEGRADABLE WATER ABSORBENT (71) Applicant: Unicharm Corporation, Ehime (JP)

(72) Inventors: Masashi Yamaguchi, Kagawa (JP); Hiroshi Uyama, Osaka (JP)

(73) Assignee: Unicharm Corporation, Ehime (JP)

( * ) Notice: Subject to any disclaimer, the term of this patent is extended or adjusted under 35 U.S.C. 154(b) by 44 days.

(21) Appl. No.: 15/527,916

(22) PCT Filed: Nov. 30, 2015

(86) PCT No.: PCT/JP2015/083631
§ 371 (c)(1),
(2) Date: May 18, 2017

(87) PCT Pub. No.: WO2016/088722
PCT Pub. Date: Jun. 9, 2016

(65) Prior Publication Data
US 2018/0311401 A1 Nov. 1, 2018

(30) Foreign Application Priority Data
Dec. 1, 2014 (JP) ................................. 2014-243371

(51) Int. Cl.
A61L 15/60 (2006.01)
B01J 20/24 (2006.01)
B01J 20/28 (2006.01)
B01J 20/30 (2006.01)
B01J 20/12 (2006.01)

(52) U.S. Cl.
CPC .............. A61L 15/60 (2013.01); B01J 20/12 (2013.01); B01J 20/24 (2013.01); B01J 20/28004 (2013.01); B01J 20/28016 (2013.01); B01J 20/3028 (2013.01); B01J 20/3085 (2013.01)

(58) Field of Classification Search
CPC .................................... B01J 20/12; B01J 20/24
See application file for complete search history.

(56) References Cited

U.S. PATENT DOCUMENTS

2005/0214541 A1    9/2005   Berrada et al.

FOREIGN PATENT DOCUMENTS

| JP | 2003-033652 A | 2/2003 |
| JP | 2006-291144 A | 10/2006 |
| JP | 2007-533780 A | 11/2007 |
| JP | 2008-254165 A | 10/2008 |
| JP | 2008-303319 A | 12/2008 |
| JP | 2009-114391 A | 5/2009 |
| WO | WO 2005/030279 A1 | 4/2005 |
| WO | WO 2007-034795 A1 | 3/2007 |
| WO | WO 2011/038374 A2 | 3/2011 |
| WO | WO 2014-162843 A1 | 10/2014 |

OTHER PUBLICATIONS

Bao Yan et al., "Synthesis and swelling behaviors of sodium carboxymethyl cellulose-g-poly(AA-co-AM-co-AMPS)/MMT superabsorbent hydrogel", Carbohydrate Polymers, vol. 84, issue 1, pp. 76-82, ISSN 0144-8617 dated Feb. 11, 2011.
International Search Report from corresponding PCT application No. PCT/JP2015/083631 dated Feb. 16, 2016 (4 pgs).
Wang Xuman et al., "Preparation of poly(y-glutamic acid)/montmorillonite superabsorbent nanocomposite", Key Engineering Materials, vols. 531-532, pp. 609-613, ISSN 1013-9826 (2013).

Primary Examiner — Peter F Godenschwager
(74) Attorney, Agent, or Firm — Brinks Gilson Lione (57) ABSTRACT Provided is a biodegradable water absorbent having high gel strength and exhibiting an excellent absorption factor and excellent liquid passage rate through a gel. A water absorbent comprising a cross-linked naturally derived polymer and a clay mineral, the water absorbent being characterized in that the cross-linked naturally derived polymer and the clay mineral form particles, the clay mineral is present in the interior of the particles, and the clay mineral content constitutes 10-100 parts by mass (when dry) relative to 100 parts by mass (when dry) of the cross-linked naturally derived polymer. It is possible to produce this water absorbent by preparing a starting material fluid in which the naturally derived polymer is dissolved and the clay mineral is dispersed, adding a cross-linking agent to the starting material fluid, and cross-linking the naturally derived polymer.

8 Claims, 4 Drawing Sheets

ABIODEGRADABLE WATER ABSORBENT

RELATED APPLICATION

This application is a 35 U.S.C. § 371 national phase filing of International Patent Application No. PCT/JP2015/083631, filed Nov. 30, 2015, through which and to which priority is claimed under 35 U.S.C. § 119 to Japanese Patent Application No. 2014-243371, filed Dec. 1, 2014, the complete disclosure of which is hereby expressly incorporated by reference.

TECHNICAL FIELD

The present invention relates to a water absorbent. More specifically, it relates to a biodegradable water absorbent obtained from a naturally derived polymer.

BACKGROUND ART

Absorbent bodies of absorbent articles such as disposable diapers and sanitary articles generally employ superabsorbent polymers (hereunder also referred to as "SAP") and pulp.

The commonly used SAP materials at the current time include synthetic polymer-based SAP such as polyacrylate-based polymers, but in recent years much attention has become focused on naturally derived SAP such as polyglutamate-based polymers, from the viewpoint of biodegradability.

For example, International Publication No. WO 2007/034795 A1 discloses a method for obtaining a biodegradable polyglutamate gel with excellent swelling and moisture retention properties, at a high yield, using a water-soluble carbodiimide and an N-hydroxysuccinic acid imide as a condensation agent and condensation adjuvant during crosslinking of poly(glutamic acid) with a polyamine.

In addition, Japanese Unexamined Patent Publication No. 2009-114391 discloses, for increased SAP gel liquid flow speed and water absorption under load, an absorbent including a water-soluble vinyl polymer and/or a hydrolyzable vinyl monomer, as well as a crosslinked polymer having a crosslinking agent as an essential structural unit, and smectite.

PRIOR ART DOCUMENTS

Patent Documents

Patent Document 1: International Publication No. WO 2007/034795 A1
Patent Document 2: Japanese Unexamined Patent Publication No. 2009-114391

DISCLOSURE OF THE INVENTION

Problems to be Solved by the Invention

According to the method disclosed in International Publication No. WO 2007/034795 A1, the poly(glutamic acid) is crosslinked with a small amount of polyamine, and therefore a gel with low crosslink density and high swelling can be obtained (paragraphs [0019] and [0033]). The obtained gel therefore has low gel strength during swelling, and upon absorption of water the gaps between gel particles collapse to form a closely contacted state, thus inhibiting continuous liquid permeability. In addition, gel blocking tends to occur, reducing the likelihood of obtaining a continuous liquid absorbing property.

The method disclosed in Japanese Unexamined Patent Publication No. 2009-114391 carries out mixing of a crosslinked manufactured by a water-soluble vinyl polymer and/or hydrolyzable vinyl polymer obtained by publicly known aqueous polymerization or reversed-phase suspension polymerization, with smectite in a later step, or polymerization of a water-soluble vinyl polymer and/or hydrolyzable vinyl monomer by publicly known aqueous polymerization or reversed-phase suspension polymerization in the presence of smectite. When the crosslinked product is mixed with a clay mineral in a later step, the mixing is with a hydrogel, which reduces the dispersibility and results in unstable quality. In addition, the clay mineral in the gel tends to be simply dispersed, reducing the improving effect on the liquid permeability and liquid absorption that is provided by increased gel strength. As regards addition of the clay mineral in the polymerization step, the structure of the clay mineral in the gel is not described and the production method is carried out according to a known polymerization method, and therefore when the clay mineral content is high it is difficult to obtain a homogeneous crosslinked product by the aggregation that occurs in the synthesis step, and since there is no resulting compound structure with hydrogel molecular chains intervening between clay layers or a structure with uniform dispersion of detached clay mineral layers, the effect of improving liquid permeability or liquid absorption due to increased gel strength is minimal.

It is an object of the present invention to provide a water absorbent that is biodegradable, has high gel strength, and has an excellent absorption factor and gel liquid flow speed.

Means for Solving the Problems

The present invention is a water absorbent comprising 100 parts by dry weight of a crosslinked naturally derived polymer and 10 to 100 parts by dry weight of a clay mineral, wherein the crosslinked naturally derived polymer and the clay mineral form a particle, and the clay mineral is present inside the particle.

The naturally derived polymer is preferably a poly(glutamic acid) or a carboxymethyl cellulose.

The clay mineral is preferably composed mainly of montmorillonite.

The naturally derived polymer preferably has a condensable functional group.

The present invention is also a method for producing a water absorbent comprising a crosslinked naturally derived polymer and a clay mineral, wherein the method comprises the steps of preparing a starting solution in which a naturally derived polymer is dissolved and a clay mineral is dispersed, and crosslinking the naturally derived polymer by adding a crosslinking agent to the starting solution.

The method also preferably comprises a step of wet-granulating a hydrogel containing the crosslinked naturally derived polymer obtained in the step of crosslinking the naturally derived polymer.

The method also preferably comprises a step of adding a water-miscible organic solvent to the wet-granulated hydrogel and dewatering the hydrogel.

The method still further preferably comprises a step of drying the dewatered hydrogel.

The crosslinking agent is preferably a polyamine or a compound having two or more epoxy groups.

The water absorbent preferably comprises 100 parts by dry weight of the crosslinked naturally derived polymer and 10 to 100 parts by dry weight of the clay mineral.

The crosslinking agent is preferably added in an amount of 0.5 to 25 parts by weight based on 100 parts by dry weight of the naturally derived polymer.

The present invention is also a water absorbent comprising a crosslinked naturally derived polymer and a clay mineral, obtained by preparing a starting solution in which a naturally derived polymer is dissolved and a clay mineral is dispersed, and adding a crosslinking agent to the starting solution to crosslink the naturally derived polymer.

The invention is also an absorbent article including the above water absorbent.

Effect of the Invention

The water absorbent of the invention is biodegradable, has high gel strength, and has an excellent absorption factor and gel liquid flow speed.

MODE FOR CARRYING OUT THE INVENTION

The present invention is a water absorbent comprising 100 parts by dry weight of a crosslinked naturally derived polymer and 10 to 100 parts by dry weight of a clay mineral, wherein the crosslinked naturally derived polymer and the clay mineral form a particle, and the clay mineral is present inside the particle.

The naturally derived polymer to be used for the invention is not particularly restricted so long as it is a polymer that is naturally derived. A naturally derived polymer is a polymer obtained by fermentation with microorganisms or a polymer extracted from a natural substance, and this is often referred to as a "biopolymer".

Specific examples of naturally derived polymers include, but are not limited to, poly(amino acid)s such as poly (glutamic acid) (hereunder, "PGA"), poly(aspartic acid), polylysine and polyarginine, as well as their salts, polysaccharides such as alginic acid, hyaluronic acid and chitosan, and chemically modified natural polymers such as carboxymethyl cellulose. Preferred naturally derived polymers are poly(glutamic acid) or carboxymethyl cellulose. The polyamino acids may also be copolymers. Also, two or more different naturally derived polymers may be used in admixture.

The naturally derived polymer may have a condensable functional group. When the crosslinking is accomplished by condensation reaction, the condensable functional groups contribute by reacting with the crosslinking agent, thereby crosslinking the naturally derived polymer. Examples of condensable functional groups include carboxyl groups and amino groups, with carboxyl groups being preferred because they also impart hydrophilicity. When the crosslinking is accomplished by addition reaction, the presence or absence of condensable functional groups does not contribute to crosslinking, but the naturally derived polymer preferably has carboxyl groups in order to exhibit high water absorption.

Since the crosslinked naturally derived polymer is to be obtained by crosslinking reaction in an aqueous solution, the naturally derived polymer is preferably hydrophilic, and is more preferably in the form of a water-soluble salt. A naturally derived polymer with a carboxyl group, for example, is preferably in the form of a metal salt such as a sodium salt or potassium salt, or an ammonium salt, amine salt or the like, while a naturally derived polymer with an amino group is preferably in the form of an inorganic acid salt such as a hydrochloride or sulfate, or an organic acid salt such as an acetate.

The molecular weight of the naturally derived polymer is not particularly restricted, but the weight-average molecular weight is preferably 10,000 to 13,000,000, more preferably 50,000 to 10,000,000 and even more preferably 300,000 to 5,000,000. If the molecular weight is too low, the number of uncrosslinked molecular chains per unit weight will increase and the amount of elution will increase, resulting in a low-strength gel. If the molecular weight is too high, the dissolved viscosity will increase, preventing homogeneous dispersion of the clay mineral or crosslinking agent.

A crosslinked naturally derived polymer is a radiation-crosslinkable product obtained by reacting a naturally derived polymer with a crosslinking agent to form chemical crosslinking, or exposing a naturally derived polymer to radiation. The crosslinking will be described below.

According to the invention, a clay mineral is a mineral that is a component of clay, and it is composed mainly of a laminar silicate mineral. Smectite group clay minerals are preferred for the clay mineral. Smectite group clay minerals include montmorillonite, beidellite and nontronite, among which montmorillonite is preferred. Bentonite is a clay composed mainly of montmorillonite and including accessory minerals such as quartz, and according to the invention, clays containing such clay minerals may also be used for the clay mineral.

In the water absorbent of the invention, the crosslinked naturally derived polymer and the clay mineral form particles. The particle shapes are not particularly restricted but are preferably spherical. The particle sizes (circle equivalent diameters of projected area) are preferably 150 to 850 μm, more preferably 200 to 600 μm and even more preferably 300 to 400 μm. If the particles are too small, the gaps between particles during swelling will be reduced and blocking will take place when they are incorporated into the absorbent body. If the particles are too large, the area-to-weight ratio will be reduced and the moisture absorption speed will be lowered. The particle sizes (circle equivalent diameters of projected area) can be measured with an electron microscope.

Figure 1:
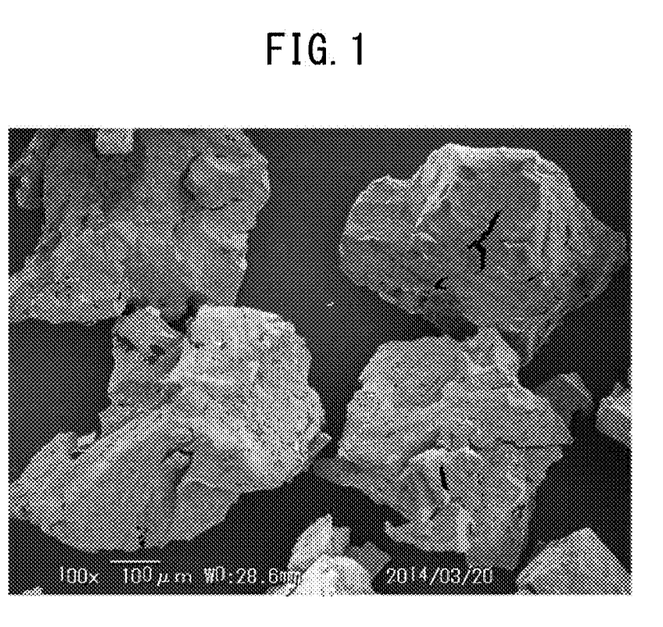
FIG. 1 is an electron micrograph showing the outer appearance of the water absorbent particles prepared in Example 2.
Figure 2:
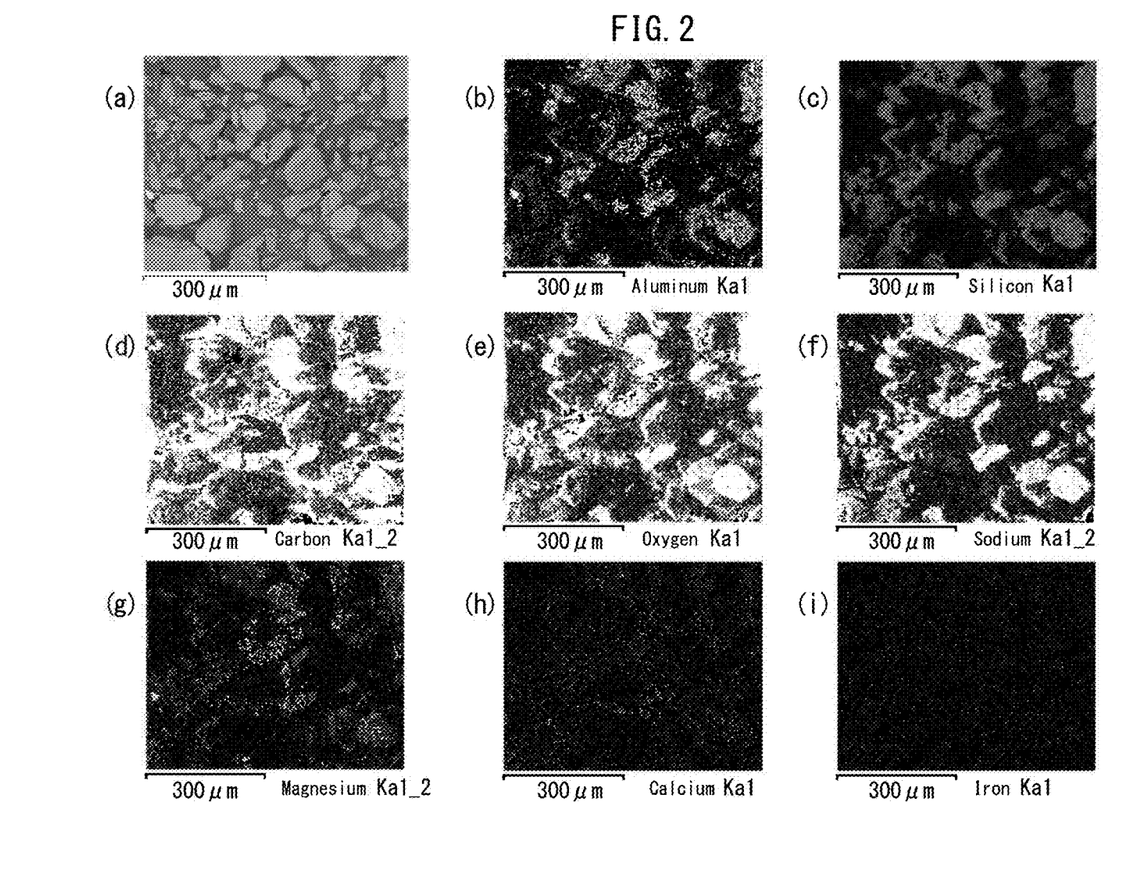
FIG. 2 is an EDX analytical photograph of a cross-section (cut surface) of the water absorbent particles prepared in Example 2.

In the water absorbent of the invention, the clay mineral is present in the particle interiors. However, it is not necessary for all of the clay mineral to be present in the particle interiors, and a portion of the clay mineral may be exposed on the particle exteriors (outside surfaces). FIG. 1 shows an electron micrograph (100× magnification) of the outer appearance of the water absorbent particles prepared in Example 2 below, and FIG. 2 shows EDX analytical photographs (250× magnification) of particle cross-sections (cut surfaces). Here it is seen that the water absorbent prepared in Example 2, the crosslinked naturally derived polymer and the clay mineral form particles, the clay mineral being present in the particle interiors.

The clay mineral, which is a laminar silicate, swells by dispersion in water and results in interlaminar opening. When a homogenizer is used for forceful dispersion, lumps are less likely to form, and therefore swelling is facilitated. When the uncrosslinked naturally derived polymer dissolves in the clay mineral dispersion, some of the molecular chains of the naturally derived polymer also become incorporated between the opened interlayer regions. Crosslinking causes some of the molecular chains of the naturally derived polymer to become immobilized in a locked state, thereby reinforcing the lattice. Since the water absorbent of the invention has some or all of the molecular chains of the naturally derived polymer inserted between the laminar silicate layers, the interlayer distance is enlarged.

Figure 3:
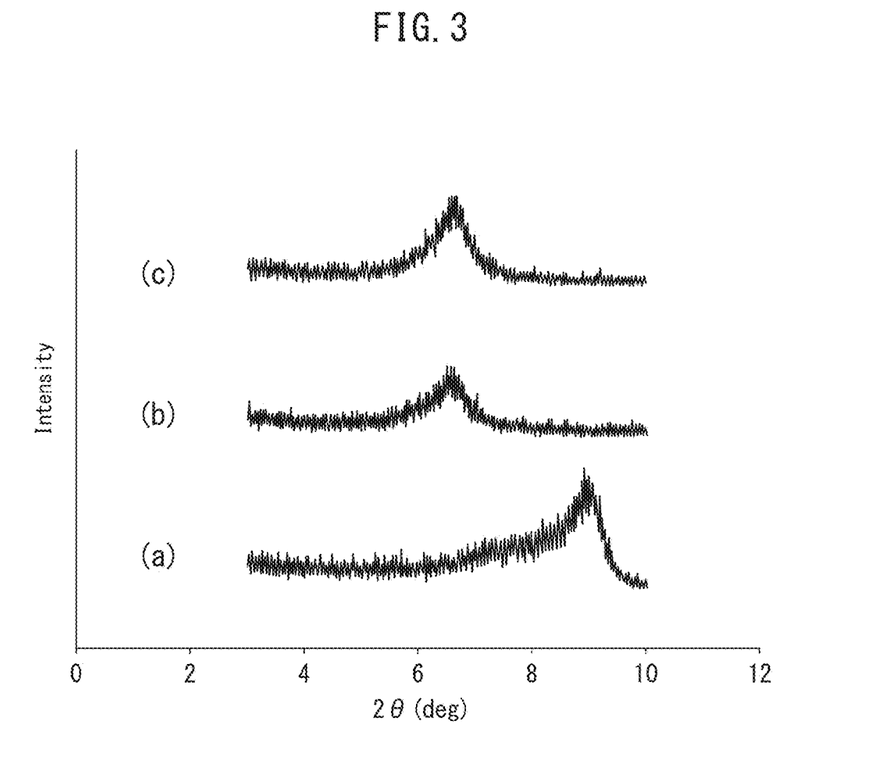
FIG. 3 is an X-ray diffraction image of a clay mineral.

FIG. 3 shows an X-ray diffraction diagram of the clay mineral. FIG. 3($a$) shows the X-ray diffraction pattern for the starting montmorillonite used in the examples, ($b$) the same for montmorillonite in the water absorbent of Example 2, and ($c$) the same for montmorillonite in the water absorbent of Example 4. Since the peaks were shifted leftward with the water absorbent ($b$) of Example 2 and the water absorbent ($c$) of the Example 4, compared to the starting montmorillonite ($a$), the interlayer regions were clearly enlarged.

The present invention increases the gel strength by addition of a clay mineral. Gel strength can be increased by a method of increasing the amount of crosslinking agent added, in which case the crosslink density is higher so that the gel strength is greater even upon absorption of water. Because this crosslinking is by chemical bonding, the crosslinking points are strong and the density is higher, which are also factors that inhibit swelling deformation. The invention exhibits an effect of increased gel strength without increasing the amount of chemical crosslinking agent. When the gel strength is increased by addition of a clay mineral as according to the invention, some of the molecular chains of the naturally derived polymer are inserted between the clay mineral layers, thereby increasing the gel strength, but since the linkages are not as strong as chemical bonds, a relative degree of freedom results compared to swelling deformation.

The clay mineral content is 10 to 100 parts by weight (when dry), preferably 10 to 70 parts by weight (when dry) and more preferably 20 to 50 parts by weight (when dry) with respect to 100 parts by weight (when dry) of the crosslinked naturally derived polymer. If the clay mineral content is too low, the reinforcing effect will be inadequate and a sufficient gel strength will not be obtained. If the clay mineral content is too high, the water absorbing property will be impaired.

A method for production of a water absorbent of the invention will now be explained.

The method for producing a water absorbent according to the invention includes a step of preparing a starting solution in which a naturally derived polymer is dissolved and a clay mineral is dispersed (hereunder also referred to as "starting solution preparation step"), and a step of adding a crosslinking agent to the starting solution and crosslinking the naturally derived polymer (hereunder also referred to as "crosslinking step").

The production method of the invention may also include one or more other steps from among a step of wet-granulating a hydrogel containing the crosslinked naturally derived polymer obtained in the step of crosslinking the naturally derived polymer (hereunder also referred to as "granulating step"), a step of adding a water-miscible organic solvent to the wet-granulated hydrogel and dewatering the hydrogel (hereunder also referred to as "dewatering step"), and a step of drying the dewatered hydrogel (hereunder also referred to as "drying step").

The starting solution preparation step may be carried out by dissolving the naturally derived polymer in water and dispersing the clay mineral. The method of dissolution and dispersion is not restricted, and it may be accomplished by adding the naturally derived polymer and clay mineral to water, and stirring the mixture. There are no restrictions on the order of dissolution and dispersion, and the starting solution may be prepared by simultaneously adding the naturally derived polymer and clay mineral to water and stirring, or alternatively the starting solution may be prepared by adding the naturally derived polymer to water and stirring to prepare a naturally derived polymer aqueous solution and then adding the clay mineral to the naturally derived polymer aqueous solution and stirring to disperse the clay mineral in the naturally derived polymer aqueous solution, or the starting solution may be prepared by adding the clay mineral to water and stirring to prepare a clay mineral dispersion, and then adding the naturally derived polymer to the clay mineral dispersion and stirring to dissolve the naturally derived polymer in the clay mineral dispersion, or the starting solution may be prepared by separately preparing a naturally derived polymer aqueous solution and a clay mineral dispersion and mixing the naturally derived polymer aqueous solution and clay mineral dispersion together; however, from the viewpoint of more uniformly dispersing the clay mineral, preferably the clay mineral dispersion is prepared first and the naturally derived polymer is dissolved to prepare the starting solution.

The starting solution includes the naturally derived polymer, the clay mineral and water.

The concentration of the naturally derived polymer in the starting solution is preferably 1 to 30 weight % (when dry), more preferably 3 to 20 weight % (when dry) and even more preferably 5 to 15 weight % (when dry). If the concentration of the naturally derived polymer is too low, the composite product yield will be low and the productivity will be poor. If the concentration of the naturally derived polymer is too high, the viscosity will increase, impairing the dispersibility of the clay mineral or crosslinking agent.

The concentration of the clay mineral in the starting solution is preferably 0.06 to 30 weight % (when dry), more preferably 0.3 to 14 weight % (when dry) and even more preferably 1 to 5 weight % (when dry).

The starting solution may also include, in addition to the naturally derived polymer, clay mineral and water, other substances (such as dispersing agents, emulsifying agents or organic solvents) in ranges that do not interfere with the effect of the invention.

The naturally derived polymer in the starting solution is then crosslinked. The crosslinking may be crosslinking by reaction of the naturally derived polymer with a crosslinking agent (chemical crosslinking) or crosslinking by exposure of the naturally derived polymer to radiation (radiation crosslinking), but chemical crosslinking is preferred from the viewpoint of crosslinking uniformity and productivity.

The step of adding the crosslinking agent to the starting solution and crosslinking the naturally derived polymer will now be described in detail.

The crosslinking agent is not particularly restricted so long as it is capable of crosslinking the naturally derived polymer.

For example, the crosslinking agent used may be a compound having two or more epoxy groups, such as ethyleneglycol diglycidyl ether, polyethyleneglycol diglycidyl ether or polypropyleneglycol diglycidyl ether.

Also, when the naturally derived polymer has a carboxyl group, the crosslinking agent used may be a compound having two or more amino groups, for example, an alkylenediamine such as 1,2-ethylenediamine, 1,3-propanediamine, 1,4-butanediamine, 1,5-heptanediamine or 1,6-hexanediamine, or diethylenetramine, triethylenetetramine, tetraethylenepentamine, pentaethylenehexamine, polyethyleneimine or the like (hereunder also referred to as "polyamine"), or an amino group-containing polymer such as polylysine, chitosan or the like.

When the naturally derived polymer has an amino group, the crosslinking agent used may be a compound having two or more carboxyl groups, such as fumaric acid, maleic acid, itaconic acid, citraconic acid or trimellitic acid, or a carboxyl group-containing polymer such as polyacrylic acid, polymethacrylic acid, poly(glutamic acid), alginic acid, hyaluronic acid or the like.

The amount of crosslinking agent used for crosslinking of the naturally derived polymer is preferably 0.5 to 25 parts by weight, more preferably 1 to 20 parts by weight and even more preferably 3 to 15 parts by weight with respect to 100 parts by weight of the naturally derived polymer. If the amount of crosslinking agent is too small, the crosslink density will tend to be lower and it can potentially be difficult to obtain a gel state. If the amount of crosslinking agent is too large, the crosslink density will tend to be higher and the degree of swelling of the obtained water absorbent can potentially be lowered.

A condensation agent or condensation aid may also be used together with the crosslinking agent. When a condensation agent or condensation aid is used it is possible to more efficiently form amide bonds.

A water-soluble carbodiimide may be mentioned as a condensation agent. A water-soluble carbodiimide is a compound having a carbodiimide group (—N=C=N—) in the molecule, the compound being water-soluble. Specific examples of water-soluble carbodiimides include 1-ethyl-3-(3-dimethylaminopropyl)carbodiimide and its salts, 1-cyclohexyl-3-(2-morpholinoethyl)carbodiimide-(meta)-p-toluenesulfuric acid and its salts, and dicyclohexylcarbodiimide, among which 1-ethyl-3-(3-dimethylaminopropyl)carbodiimide hydrochloride and 1-cyclohexyl-3-(2-morpholinoethyl)carbodiimide-(meta)-p-toluenesulfuric acid salts are preferred.

The amount of condensation agent used may be 0 to 50 mol, preferably 1 to 40 mol and more preferably 2 to 30 mol with respect to 1 mol of the crosslinking agent used.

An N-hydroxyimide may be mentioned as a condensation aid. An N-hydroxyimide is a compound having an N-hydroxyimide group (—(C=O)—(N—OH)—(C=O)—) in the molecule. Such compounds are represented by the following general formula.

Here, $R^1$ and $R^2$ may bond together to form a ring structure. Preferred is a compound wherein $R^1$ and $R^2$ bond so that the two carbons in $R^1$ and $R^2$ form a 5-membered ring with the N-hydroxyimide group. Also, the N-hydroxyimide is preferably water-soluble. Specific examples of N-hydroxyimides that can be used include N-hydroxysuccinic acid imide, N-hydroxymaleic acid imide, N-hydroxyhexahydrophthalic acid imide, N,N'-dihydroxycyclohexanetetracarboxylic acid imide, N-hydroxyphthalic acid imide, N-hydroxytetrabromophthalic acid imide, N-hydroxytetrachlorophthalic acid imide, N-hydroxychlorendic acid imide, N-hydroxyhymic acid imide, N-hydroxytrimellitic acid imide, N,N'-dihydroxypyromellitic acid imide and N,N'-dihydroxynaphthalenetetracarboxylic acid imide. Preferred among these N-hydroxyimides is N-hydroxysuccinic acid imide.

The amount of condensation aid used may be 0 to 50 mol, preferably 1 to 40 mol and more preferably 2 to 30 mol with respect to 1 mol of the crosslinking agent used. The amount of condensation aid used is preferably equimolar with the amount of condensation agent used.

There are no particular restrictions on the conditions for the crosslinking step. It may be carried out at room temperature or with heating. If the temperature is too low, however, a very long time will be required for the crosslinking reaction, and therefore heating is preferably conducted. The temperature for the crosslinking step is preferably 10 to 100° C., more preferably 15 to 70° C. and even more preferably 20° C. to 50° C. If it is too high, the naturally derived polymer will tend to decompose. The step is therefore preferably carried out at near room temperature. The pH during the crosslinking reaction is not particularly restricted, but is preferably 5 to 12, more preferably 6 to 11 and even more preferably 7 to 10.

The reaction time for the crosslinking step is preferably 5 minutes to 6 hours, more preferably 10 minutes to 3 hours and even more preferably 20 minutes to 2 hours. During the crosslinking reaction, the reaction mixture may be stirred if necessary, or it may be stationed at rest. It is preferably stationed at rest. After a sufficient period of time has passed for the crosslinking reaction, a gel is obtained in the reaction mixture. The reaction mixture is washed with water (preferably ion-exchanged water or distilled water) to remove the unreacted crosslinking agent, condensation agent and condensation aid in the reaction mixture, to obtain a gel in which the naturally derived polymer is crosslinked with the crosslinking agent.

Next, a hydrogel containing the crosslinked naturally derived polymer obtained in the crosslinking step is subjected to wet-granulating (granulating step). In this step, the hydrogel is granulated to a desired size in a wetted state (i.e. wet-granulated). The granulation is preferably first coarse granulation, followed by main granulation. The coarse granulation is carried out by, for example, stirring the hydrogel obtained from the crosslinking reaction, using a spatula or the like. In the main granulation, the hydrogel is granulated using an apparatus suitable for wet-granulation, such as a homomixer, homogenizer, bead mill, pipe mixer or the like. As used herein, "granulated hydrogel" refers to hydrogel particles. The mean particle size of the hydrogel particles may be appropriately set according to the purpose of use of the dry gel powder that is to be finally obtained, or according to the apparatus used for granulation, but it is preferably 10 μm to 10 mm and more preferably 100 μm to 3 mm.

When the hydrogel viscosity is high or granulation is difficult, a water-miscible organic solvent may be added, as described below. Specifically, granulation may be carried out after adding a water-miscible organic solvent. By adding a water-miscible organic solvent, the hydrogel becomes dewatered and reduced in volume (shrunken), the viscosity of the dispersion during the wet-granulation is lowered, and the flow property is restored. Even when the viscosity has increased during granulation, the water-miscible organic solvent may be added during the procedure and granulation continued. The wet-granulating step and the subsequent dewatering step may thus be carried out simultaneously.

When a naturally derived polymer with a carboxyl group is used as the starting material, the carboxyl group portion of the naturally derived polymer is converted to a water-soluble salt form such as a sodium salt to prepare a hydrogel, as mentioned above. However, when a hydrogel in salt form is worked into a dry gel powder, it absorbs moisture in the atmosphere, potentially causing coalescence of the powder. After preparing the hydrogel, therefore, an inorganic acid or organic acid may be added to convert a portion of the salt form to the free acid form. A dry gel powder obtained from a hydrogel in free acid form has lower hygroscopicity than a dry gel powder in salt form, and therefore the powder is resistant to coalescence. Examples of inorganic acids and organic acids include sulfuric acid, hydrochloric acid, nitric acid and p-toluenesulfonic acid. An inorganic acid or organic acid is preferably added to the hydrogel particle by mixing with the water-miscible organic solvent. When an inorganic acid or organic acid is added, the hydrogel is neutralized homogeneously, yielding hydrogel particles in a homogeneous free acid form.

Next, a water-miscible organic solvent is added to the wet-granulated hydrogel and the hydrogel is dewatered (dewatering step). When the hydrogel particles are dipped into the water-miscible organic solvent, the water in the hydrogel particles is released into the water-miscible organic solvent. The hydrogel particles, being dewatered, sometimes shrink to fine particle sizes. In addition, unwanted substances such as the unreacted crosslinking agent used for crosslinking of the naturally derived polymer, or the condensation agent and condensation aid, are released from the hydrogel particles together with water.

The water-miscible organic solvent is not particularly restricted. Examples that may be mentioned include lower alcohols such as methanol, ethanol, isopropanol, n-propanol and tertiary butanol, glycol ethers such as ethyleneglycol monomethyl ether, ethyleneglycol monoethyl ether, ethyleneglycol monoisopropyl ether, propyleneglycol monomethyl ether and propyleneglycol monoethyl ether, and acetone. Preferred among these are methanol, ethanol, isopropanol and acetone. These water-miscible organic solvents may be used alone or in mixtures of two or more, or two or more different solvents may be added successively depending on the dispersed state.

Dipping of the hydrogel particles into the water-miscible organic solvent may be repeated several times. In this case, the solvent containing water that has been released from the hydrogel particles is removed by filtration or decantation, and fresh water-miscible organic solvent is added to the hydrogel particles. By repeating the dipping several times in this manner, the hydrogel particles are further dewatered and shrink, resulting in fine particles with an extremely low water content. When dipping is repeated several times, a different water-miscible organic solvent may even be used for each dipping.

The amount of water-miscible organic solvent used will differ depending on its type, and on the amount of water and other factors during preparation of the hydrogel, but for a single dipping, it is preferably a 1-fold volume (equivolume) to 20-fold volume, more preferably a 2-fold volume to 10-fold volume, and even more preferably a 3-fold volume to 7-fold volume, with respect to the hydrogel.

The time for dipping of the hydrogel particles in the water-miscible organic solvent will differ depending on the type of solvent and its amount, for example, but for a single dipping, it is preferably 1 minute to 2 hours, more preferably 2 minutes to 1 hour and even more preferably 3 minutes to 30 minutes, from the standpoint of manageability.

If necessary, the hydrogel particles may be rinsed with an appropriate fluid after dipping in the water-miscible organic solvent.

The dewatered hydrogel is then dried (drying step). The hydrogel particles obtained after the dewatering step have a low water content, containing virtually no moisture. Thus, the water-miscible organic solvent may be removed by filtration or decantation, and then blow air-drying or stationary drying carried out at room temperature to 150° C., more preferably 35° C. to 125° C. and even more preferably 50° C. to 100° C., to obtain a dry gel powder. Since the hydrogel particles are therefore not exposed to harsh drying conditions, the particles do not coalesce together during the drying.

The particle diameter of the obtained dry gel powder can be determined in consideration of the intended use of the dry gel powder, for example, and it is not particularly restricted. That is, a dry gel powder can be obtained having a desired particle diameter, depending on the granulating apparatus (homomixer, homogenizer or the like) and the granulating force used for the granulating step.

Generally speaking, when a polymer fails to maintain a network structure (gel state), the polymer will dissolve when it is immersed in water. However, the dry gel powder obtained by the method described above, when dipped in water, swells without being dissolved, thus regenerating a hydrogel. Consequently, the dry gel powder obtained by this method maintains its network structure (gel state).

EXAMPLES

Example 1

After dispersing 6.04 g of montmorillonite (KUNIPIA F, manufactured by Kunimune Industries Co., Ltd.) in 722 g of ion-exchanged water, a homogenizer (AHG-160D, shaft generator HT1018, manufactured by As One Corp.) was used for dispersion at 1000 rpm for 3 minutes. Into this there was added and dissolved 54.4 g of poly(γ-glutamic acid) (Na-type, molecular weight: 2,000,000, manufactured by Bioleaders Corp.) (hereunder also, "PGA-Na") (360 millimoles, with PGA-Na unit molecular weight as 151) (PGA-Na:montmorillonite=90:10 (weight ratio)). The PGA-Na concentration was 7%. Upon then adding 1.11 g (10.8 millimoles) of diethylenetriamine (hereunder also, "DETA") (manufactured by Wako Pure Chemical Industries, Ltd.), 3.73 g (32.4 millimoles) of N-hydroxysuccinic acid imide (hereunder also, "NHS") (manufactured by Wako Pure Chemical Industries, Ltd.) and 6.21 g (32.4 millimoles) of 1-ethyl-3-(3-dimethylaminopropyl)carbodiimide hydrochloride (hereunder also, "EDC.HCl") (manufactured by Wako Pure Chemical industries, Ltd.) and stirring the mixture, a hydrogel was obtained after approximately 1 minute and 40 seconds. After 30 minutes from completion of the addition, the obtained opaque hydrogel was coarsely granulated with a spatula. Next, 20 g of methanol (manufactured by Wako Pure Chemical Industries, Ltd.) was added to the coarsely granulated hydrogel, and a homogenizer (AHG-160D, shaft generator HT1018, manufactured by As One Corp.) was used for wet-granulation under 750 rpm conditions. When the dispersion was allowed to stand after the wet-granulation, a semi-transparent hydrogel particle precipitated, the solvent was removed by decantation, another 20 g of methanol was added, and the mixture was stirred. This series of steps was repeated, carrying out dewatering until the hydrogel particles shrank and became white particles. The dewatered particles were blow air-dried under conditions of 70° C., 90 minutes, to obtain a dry gel powder water absorbent.

Example 2

A water absorbent was prepared by the same procedure as Example 1, except for using 12.1 g of montmorillonite, 642 g of ion-exchanged water, 48.3 g of PGA-Na (PGA-Na:montmorillonite=80:20 (weight ratio)), 0.99 g (9.6 millimoles) of DETA, 3.31 g (28.8 millimoles) of NHS and 5.52 g (28.8 millimoles) of EDC.HCl.

Example 3

A water absorbent was prepared by the same procedure as Example 1, except for using 18.1 g of montmorillonite, 562 g of ion-exchanged water, 42.3 g of PGA-Na (PGA-Na:montmorillonite=70:30 (weight ratio)), 0.87 g (8.4 millimoles) of DETA, 2.90 g (25.2 millimoles) or NHS and 4.83 g (25.2 millimoles) of EDC.HCl.

Example 4

A water absorbent was prepared by the same procedure as Example 1, except for using 24.2 g of montmorillonite, 481.5 g of ion-exchanged water, 36.2 g of PGA-Na (PGA-Na:montmorillonite=60:40 (weight ratio)), 0.75 g (7.2 millimoles) of DETA, 2.49 g (21.6 millimoles) of NHS and 4.14 g (21.6 millimoles) of EDC.HCl.

Example 5

A water absorbent was prepared by the same procedure as Example 1, except that the montmorillonite was changed to bentonite ("BENGEL HV" by Hojun Co., Ltd.).

Comparative Example 1

A water absorbent was prepared by the same procedure as Example 1, except for using 3.02 g or montmorillonite, 762 g of ion-exchanged water, 57.4 g of PGA-Na (PGA-Na:montmorillonite=95:5 (weight ratio)), 1.18 g (11.4 millimoles) of DETA, 3.94 g (34.2 millimoles) of NHS and 6.56 g (34.2 millimoles) of EDC.HCl.

Comparative Example 2

A water absorbent was prepared by the same procedure as Example 2, except that montmorillonite was not added.

Comparative Example 3

After dispersing 1.0 g of montmorillonite in 300 g of ion-exchanged water, a homogenizer (AHG-160D, shaft generator HT1018, manufactured by As One Corp.) was used for dispersion at 1000 rpm for 3 minutes. A 19.0 g portion of the dry gel powder obtained in Comparative Example 2 (PGA-Na:montmorillonite=95:5 (weight ratio)) was added, and kneading was continued for 3 minutes with a homogenizer. Next, 20 g of methanol (manufactured by Wako Pure Chemical Industries, Ltd.) was added, and a homogenizer (AHG-160D, shaft generator HT1018, manufactured by As One Corp.) was used for wet-granulation under conditions of 750 rpm. When the dispersion was allowed to stand after the wet-granulation, a semi-transparent hydrogel particle precipitated, the solvent was removed by decantation, another 20 g of methanol was added, and the mixture was stirred. This series of steps was repeated, carrying out dewatering until the hydrogel particles shrank and became white particles. The dewatered particles were blow air-dried under conditions of 70° C., 90 minutes, to obtain a dry gel powder water absorbent.

Comparative Example 4

A water absorbent was prepared by the same procedure as Comparative Example 3, except for using 2.0 g of montmorillonite and 18.0 g of the dry gel powder water absorbent obtained in Comparative Example 2 (PGA-Na:montmorillonite=90:10 (weight ratio)).

Comparative Example 5

A water absorbent was prepared by the same procedure as Comparative Example 3, except for using 6.0 g of montmorillonite and 14.0 g of the dry hydrogel powder obtained in Comparative Example 2 (PGA-Na:montmorillonite=70:30 (weight ratio)).

Example 6

After dispersing 3.90 g of bentonite (KUNIBOND, manufactured by Kunimune Industries Co., Ltd.) in a sodium hydroxide aqueous solution prepared by dissolving 7.76 g of NaOH in 194.1 g of ion-exchanged water, a homogenizer (AHG-160D, shaft generator HT1018, manufactured by As One Corp.) was used for dispersion at 1000 rpm for 3 minutes. Into this there was added and dissolved 35.0 g of carboxymethyl cellulose (Na-type, F800FC, manufactured by Nippon Paper Group, Inc.) (hereunder also, "CMC-Na") (CMC-Na:bentonite=90:10 (weight ratio)). The CMC-Na concentration was 15 weight %. After adding 735 µL of ethyleneglycol diglycidyl ether (hereunder also, "EGDE") (manufactured by Nagase Chemtech) and stirring the mixture, crosslinking reaction was performed at 70° C. for 15 hours. The obtained hydrogel was coarsely granulated with a spatula, and then a 3-fold amount of acetone (manufactured by Wako Pure Chemical Industries, Ltd.) was added to the coarsely granulated hydrogel and a homogenizer (same as above) was used for dewatering and wet-granulating under 750 rpm condtions. The gel was filtered and then placed in a 3-fold amount of water:acetone (70:30) and stirred for washing of the gel while partially swelling it. After finally dewatering it again with acetone alone, it was dried for 1.5 hours in a 70° C. oven to obtain a dry gel powder water absorbent. The obtained synthetic powder was sieved to separate off the 150-750 µm portion, thereby obtaining the desired water absorbent.

Example 7

A water absorbent was prepared by the same procedure as Example 6, except for using 8.8 g of bentonite (CMC-Na:bentonite=80:20 (weight ratio)).

Example 8

A water absorbent was prepared by the same procedure as Example 6, except for using 15.0 g of bentonite (CMC-Na:bentonite=70:30 (weight ratio)).

Example 9

A water absorbent was prepared by the same procedure as Example 6, except for using 23.3 g of bentonite (CMC-Na:bentonite=60:40 (weight ratio)).

Example 10

A water absorbent was prepared by the same procedure as Example 6, except that the 3.9 g of bentonite was changed to 15.0 g of montmorillonite (KUNIPIA F by Kunimune Industries Co., Ltd.) (CMC-Na:montmorillonite=70:30 (weight ratio)).

Comparative Example 6

A water absorbent was prepared by the same procedure as Example 6, except that bentonite was not added.

Comparative Example 7

After dispersing 1.0 g of bentonite (KUNIBOND, manufactured by Kunimune Industries Co., Ltd.) in 300.0 g of ion-exchanged water, a homogenizer (AHG-160D, shaft generator HT1018, manufactured by As One Corp.) was used for dispersion at 1000 rpm for 3 minutes. A 19.0 g portion of the dry gel powder obtained in Comparative Example 6 (CMC-Na:bentonite=95:5 (weight ratio)) was added, and kneading was continued for 3 minutes with a homogenizer. Next, a 3-fold amount of acetone (manufactured by Wako Pure Chemical Industries, Ltd.) was added and a homogenizer (same as above) was used for dewatering and wet-granulating under 750 rpm conditions. The gel was filtered and then placed in a 3-fold amount of water:acetone (70:30) and stirred for washing of the gel while partially swelling it. After finally dewatering it again with acetone alone, it was dried for 1.5 hours in a 70° C. oven to obtain a dry gel powder water absorbent. The obtained synthetic powder was sieved to separate off the 150-750 µm portion, thereby obtaining the desired water absorbent.

Comparative Example 8

A water absorbent was prepared by the same procedure as Comparative Example 7, except for using 2.0 g of bentonite and 18.0 g of the dry gel powder water absorbent obtained in Comparative Example 6 (CMC-Na:bentonite=90:10 (weight ratio)).

Comparative Example 9

A water absorbent was prepared by the same procedure as Comparative Example 7, except for using 6.0 g of bentonite and 14.0 g of the dry gel powder water absorbent obtained in Comparative Example 6 (CMC-Na:bentonite=70:30 (weight ratio)).

Comparative Example 10

After dispersing 15.0 g of montmorillonite (KUNIPIA F, manufactured by Kunimune Industries Co., Ltd.) in 140.0 g of ion-exchanged water, a homogenizer (AHG-160D, shaft generator HT1018, manufactured by As One Corp.) was used for dispersion at 1000 rpm for 3 minutes. After adding 12.2 g of acrylic acid (manufactured by Wako Pure Chemical Industries, Ltd.), 47.8 g of sodium acrylate (manufactured by Wako Pure Chemical Industries, Ltd.) and 0.03 g of N,N'-methylenebisacrylamide (manufactured by Wako Pure Chemical Industries, Ltd.), the mixture was stirred, producing aggregation to form a gel. Thereafter, 0.02 g of ammonium persulfate (manufactured by Wako Pure Chemical Industries, Ltd.) failed to uniformly mix, and even after reaction was conducted under conditions of 70° C. for 6 hours, it was not possible to obtain a uniform crosslinked product.

[Evaluation of Water Absorbent]

The water absorbents prepared in the examples and comparative examples were measured for water absorbent gel strength, absorption factor and gel liquid flow speed. The measurement results are shown in Table 1 and Table 2.

The methods for measuring each of the evaluated properties were as follows.

[Gel Strength Measurement Method]

(1) A bag (10×20 cm) is prepared using a 250 mesh nylon net (N-NO.250HD by NBC Industry), and a 1.0 g sample of the water absorbent is placed in it.

(2) After placing 2 L of physiological saline in a beaker, the prepared sample-containing nylon net is dipped therein and allowed to stand for 1 hour.

(3) The bag is raised up, and the short sides of the bag are clamped with clothespins and allowed to hang for 15 minutes of draining.

(4) The sample is raised up and dewatered with a centrifugal separator (150G-90s).

(5) A 10.0 g portion of the sample is placed in a PP tube with a diameter of 27 mm (NEW PP sample tube No.5, 22 mL, manufactured by Maruemu Corp.).

(6) A mesh with a diameter of 25 mm is placed on the sample.

(7) The mesh is pressed with a digital force gauge (penetration speed: 1 mm/s).

(8) The start point is the point where movement begins from the 3rd decimal place according to the value measured by the digital force gauge, and the numerical value for the maximum load when the gel has been pressed for 10 seconds (10 mm) is read off and is recorded as the gel strength.

[Absorption Factor Measurement Method]

The absorption factor of the water absorbent was measured by a non-pressure "DW" method (Demand Wettability method). The absorption factor is a measure of the continuous liquid absorption, with a higher absorption factor corresponding to more excellent continuous liquid absorption.

(Measuring Apparatus)

Figure 4:
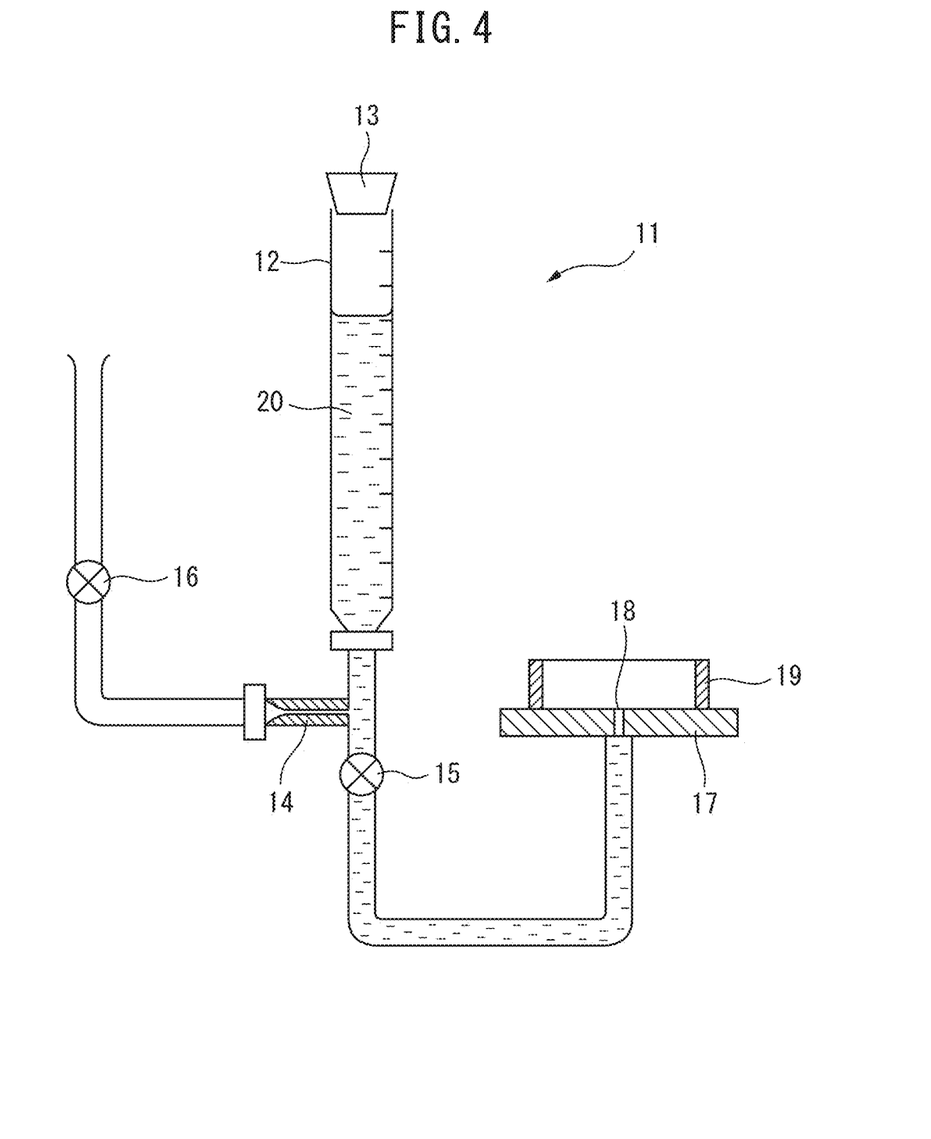
FIG. 4 is a schematic diagram of a DW apparatus to be used for measurement of the absorption factor.

The DW apparatus (Demand Wettability apparatus, manufactured by Taiyo Create Co., Ltd., using 100 mL burette) shown in FIG. 4 is used. In the drawing, 11 is the DW apparatus, 12 is the burette, 13 is a rubber stopper, 14 is an air inlet tube, 15 is a cock, 16 is a cock, 17 is a support plate, 18 is a liquid outlet, 19 is a cylinder and 20 is a test solution.

(Test Solution Preparation)

The test solution used is a 0.9% sodium chloride aqueous solution. The 0.9% sodium chloride aqueous solution is prepared in the following manner. A 3 liter beaker is placed on an electronic scale (after 0 resets), and ion-exchanged water is added to 27.0 g of sodium chloride (reagent grade A) to 3000.0 g. The mixture is then stirred to dissolution of the sodium chloride to prepare a test solution. The test solution is allowed to stand in an atmosphere at 20° C.×65% RH, and the liquid temperature of the test solution is brought to 20° C. ±1° C.

(Measuring Environment)

The measurement is conducted in an atmosphere of 20° C.×65% RH (in a steady temperature and humidity room).

(Measuring Procedure)

(1) The test solution 20 is added to higher than point 0, with both cocks 15, 16 of the DW apparatus 11 closed off, and the rubber stopper 13 is placed over the burette 12 to seal it.

(2) After placing filter paper on the liquid outlet 18 of the support plate 17, both cocks 15, 16 were opened, and the liquid level was matched to point 0 while suctioning out the liquid flowing out from the liquid outlet 18 with the filter paper. After preparation, the cock 15 was closed.

(3) A 250 mesh nylon net (N-NO.250HD by NBC Industry) is cut to 100×100 mm and placed on the liquid outlet 18.

(4) A cylinder 19 with a diameter of 30 mm is at the center section of the nylon net, and 1.00 g of the water absorbent sample is placed therein and the cylinder 19 is gently shaken to form a flat surface.

(5) The cock 15 is opened, and a stopwatch is started simultaneously when air bubbles have begun to exit.

(6) The scale V of the burette 12 is read off after an elapse of 5 minutes.

(7) The absorption factor (mL/g) is calculated by the following formula.

Absorption factor $(mL/g) = V(mL)/1.00(g)$

[Gel Liquid Flow Speed Measurement Method]

(1) After placing 0.1 g of water absorbent sample in a beaker containing 50 mL of physiological saline, it is impregnated for 30 minutes to complete swelling. The composition of the physiological saline used for this measuring method is a 0.9% sodium chloride aqueous solution.

(2) The sample swelled in (1) above is poured, together with physiological saline, into a plastic cylinder (inner diameter: 26 mm, length: 80 mm) having a mesh stretched over the bottom side. (The physiological saline drains through the mesh.)

(3) Another plastic cylinder (outer diameter: 25 mm, inner diameter: 20 mm, length: 120 mm, weight: 28 g) having a mesh stretched over the bottom side is inserted into the cylinder of (2) above.

(4) A 30 g portion of physiological saline is added at once through the top of the inner cylinder. The liquid volume is increased as appropriate if more than 30 g has passed through.

(5) The amount A (g) of physiological saline that has passed through the gel in 30 seconds is measured.

(6) The gel liquid flow speed (g/min) is calculated by the following formula.

Gel liquid flow speed $(g/min) = A(g)/0.5(min)$

The gel liquid flow speed is a measure of the continuous liquid permeability, with a greater gel liquid flow speed corresponding to more excellent continuous liquid permeability.

TABLE 1

|  | Example 1 | Example 2 | Example 3 | Example 4 | Example 5 | Comp. Ex. 1 | Comp. Ex. 2 | Comp. Ex. 3 | Comp. Ex. 4 | Comp. Ex. 5 |
|---|---|---|---|---|---|---|---|---|---|---|
| PGA-Na (g) | 54.4 | 48.3 | 42.3 | 36.2 | 54.4 | 57.4 | 48.3 | — | — | — |
| Clay mineral (g) | 6.04 | 12.1 | 18.1 | 24.2 | 6.04 | 3.02 | — | 1.0 | 2.0 | 6.0 |
| Water (g) | 722 | 642 | 562 | 481.5 | 722 | 762 | 642 | 300 | 300 | 300 |
| DETA (g) | 1.11 | 0.99 | 0.87 | 0.75 | 1.11 | 1.18 | 0.99 | — | — | — |
| NHS (g) | 3.73 | 3.31 | 2.90 | 2.49 | 3.73 | 3.94 | 3.31 | — | — | — |
| EDC•HCl (g) | 6.21 | 5.52 | 4.83 | 4.14 | 6.21 | 6.56 | 5.52 | — | — | — |
| Hydrogel of Comp. Ex. 2 (g) | — | — | — | — | — | — | — | 19.0 | 18.0 | 14.0 |
| Gel strength (kg) | 0.40 | 0.50 | 0.55 | 0.72 | 0.45 | 0.30 | 0.22 | 0.25 | 0.29 | 0.34 |
| Absorption factor (mL/g) | 24.0 | 32.7 | 42.9 | 34.2 | 16.3 | 8.8 | 2.1 | 6.7 | 8.4 | 6.0 |
| Gel liquid flow speed (g/min) | 13.0 | 20.7 | 28.3 | 33.1 | 13.6 | 2.0 | 0.4 | 0.6 | 2.8 | 5.1 |

TABLE 2

|  | Example 6 | Example 7 | Example 8 | Example 9 | Example 10 | Comp. Ex. 6 | Comp. Ex. 7 | Comp. Ex. 8 | Comp. Ex. 9 |
|---|---|---|---|---|---|---|---|---|---|
| CMC-Na (g) | 35.0 | 35.0 | 35.0 | 35.0 | 35.0 | 35.0 | — | — | — |
| Clay mineral (g) | 3.9 | 8.8 | 15.0 | 23.3 | 15.0 | — | 1.0 | 2.0 | 6.0 |
| Water (g) | 194.1 | 194.1 | 194.1 | 194.1 | 194.1 | 1194.1 | 300 | 300 | 300 |
| EGDE (µL) | 735 | 735 | 735 | 735 | 735 | 735 | — | — | — |
| NaOH (g) | 7.76 | 7.76 | 7.76 | 7.76 | 7.76 | 7.76 | — | — | — |
| Hydrogel of Comp. Ex. 6 (g) | — | — | — | — | — | — | 19.0 | 18.0 | 14.0 |
| Gel strength (kg) | 0.42 | 0.55 | 0.58 | 0.72 | 0.49 | 0.23 | 0.29 | 0.35 | 0.38 |
| Absorption factor (mL/g) | 16.6 | 22.0 | 32.0 | 31.1 | 29.8 | 3.7 | 5.5 | 7.0 | 9.8 |
| Gel liquid flow speed (g/min) | 19.7 | 26.5 | 49.1 | 62.2 | 20.7 | 1.5 | 3.1 | 5.7 | 9.0 |

TABLE 3

|  | Comp. Example 10 |
|---|---|
| Acrylic acid (g) | 12.2 |
| Sodium acrylate (g) | 47.8 |
| Clay mineral (g) | 15.0 |
| Water (g) | 140.0 |
| N,N'-Methylenebisacrylamide (g) | 0.03 |
| Ammonium persulfate (g) | 0.20 |
| Gel strength (kg) | — |
| Absorption factor (mL/g) | — |
| Gel liquid flow speed (g/min) | — |

The water absorbents of the examples had high gel strength due to the reinforcing effect of the clay mineral, and were also resistant to blocking and therefore exhibited a high absorption factor, i.e. a high continuous liquid drawing property, as well as a high gel liquid flow speed, i.e. high continuous liquid permeability.

When no clay mineral was added (Comparative Examples 2 and 6), or when the clay mineral content was low (Comparative Example 1), or when the clay mineral was added after crosslinking of the naturally derived polymer (Comparative Examples 3 to 5 and 7 to 9), neither the liquid drawing property nor the liquid permeability were significantly improved.

Moreover, when acrylic acid was used as the starting material, it was found that addition of the clay mineral to a clay mineral content that produces a high effect according to the invention (20 weight %) results in aggregation by the clay in the synthesis process, such that a uniform gel fails to form (Comparative Example 10).

INDUSTRIAL APPLICABILITY

The water absorbent of the invention has high gel strength and an excellent absorption factor and gel liquid flow speed, and it can therefore be suitably used as a starting material to form an absorbent body for an absorbent article such as a disposable diaper or sanitary napkin.

REFERENCE SIGNS LIST

11 DW apparatus
12 Burette
13 Rubber stopper
14 Air inlet tube
15 Cock
16 Cock
17 Support plate
18 Liquid outlet
19 Cylinder
20 Test solution

The invention claimed is:

1. A method for producing a water absorbent comprising a crosslinked naturally derived polymer and a clay mineral, and having a gel strength of 0.40 to 0.72 kg and an absorption factor of 16.3 to 42.9 mL/g, wherein the method comprises the steps of preparing a starting solution in which a naturally derived polymer is dissolved and a clay mineral is dispersed, and crosslinking the naturally derived polymer by adding a crosslinking agent, a condensation agent and a condensation aid to the starting solution, wherein the naturally derived polymer is a poly(γ-glutamic acid); the crosslinking agent is diethylenetriamine; the condensation agent is 1-ethyl-3-(3-dimethylaminopropyl)carbodiimide hydrochloride; the condensation aid is N-hydroxysuccinimide; an amount of the clay mineral is 10 to 100 parts by dry weight of based on 100 parts by dry weight of the naturally derived polymer; the naturally derived polymer has a molecular weight of 300,000 to 5,000,000; a concentration of the naturally derived polymer in the starting solution is 5 to 15 percent by dry weight; an amount of the crosslinking agent is 0.5 to 25 parts by weight based on 100 parts by dry weight of the naturally derived polymer; an amount of the condensation agent is 2 to 30 mol based on 1 mol of the crosslinking agent; and an amount of the condensation aid is 2 to 30 mol based on 1 mol of the crosslinking agent.

2. The method according to claim 1, further comprising a step of wet-granulating a hydrogel containing the crosslinked naturally derived polymer obtained in the step of crosslinking the naturally derived polymer.

3. The method according to claim 2, further comprising a step of adding a water-miscible organic solvent to the wet-granulated hydrogel and dewatering the hydrogel.

4. The method according to claim 3, further comprising a step of drying the dewatered hydrogel.

5. The method according to claim 1, wherein the water absorbent has a particle size, measured as a circle equivalent diameter of projected area, of 300 to 400 μm.

6. The method according to claim 2, wherein the water absorbent has a particle size, measured as a circle equivalent diameter of projected area, of 300 to 400 μm.

7. The method according to claim 3, wherein the water absorbent has a particle size, measured as a circle equivalent diameter of projected area, of 300 to 400 μm.

8. The method according to claim 4, wherein the water absorbent has a particle size, measured as a circle equivalent diameter of projected area, of 300 to 400 μm.

* * * * *